US009220444B2

(12) United States Patent
Russell

(10) Patent No.: US 9,220,444 B2
(45) Date of Patent: Dec. 29, 2015

(54) SYSTEM METHOD AND DEVICE FOR DETERMINING THE RISK OF DEHYDRATION

(75) Inventor: Brian Russell, Crownsville, CT (US)

(73) Assignee: Zephyr Technology Corporation, Annapolis, MD (US)

( * ) Notice: Subject to any disclaimer, the term of this patent is extended or adjusted under 35 U.S.C. 154(b) by 366 days.

(21) Appl. No.: 13/154,317

(22) Filed: Jun. 6, 2011

(65) Prior Publication Data
US 2012/0143019 A1 Jun. 7, 2012

Related U.S. Application Data

(60) Provisional application No. 61/352,293, filed on Jun. 7, 2010.

(51) Int. Cl.
A61B 5/00 (2006.01)
A61B 5/11 (2006.01)
G06F 19/00 (2011.01)
A61B 5/0205 (2006.01)
A61B 5/145 (2006.01)

(52) U.S. Cl.
CPC ............ *A61B 5/1116* (2013.01); *A61B 5/0205* (2013.01); *A61B 5/1118* (2013.01); *A61B 5/14507* (2013.01); *A61B 5/6823* (2013.01); *A61B 5/6831* (2013.01); *A61B 5/72* (2013.01); *G06F 19/34* (2013.01); *G06F 19/3418* (2013.01); *G06F 19/3431* (2013.01); *A61B 5/02055* (2013.01); *A61B 2560/0242* (2013.01)

(58) Field of Classification Search
CPC ... A61B 5/0205; A61B 5/0524; A61B 5/4035
See application file for complete search history.

(56) References Cited

U.S. PATENT DOCUMENTS

| 5,865,760 | A  | * | 2/1999  | Lidman et al. | 600/509 |
| 6,390,986 | B1 | * | 5/2002  | Curcie et al. | 600/485 |
| 7,333,854 | B1 | * | 2/2008  | Brewer et al. | 607/18  |
| 7,840,275 | B2 | * | 11/2010 | Verhoef       | 607/60  |
| 7,848,811 | B2 | * | 12/2010 | Moon et al.   | 607/19  |

(Continued)

OTHER PUBLICATIONS

Schroeder, C. et al.; "Water Drinking Acutely Improves Orthostatic Tolerance in Healthy Subjects"; Circulation. 2002; 106: 2806-2811.*

(Continued)

*Primary Examiner* — William Thomson
*Assistant Examiner* — Marie Archer

(57) ABSTRACT

A system, device and method of determining the probability of dehydration of a person is provided. In one embodiment, the method comprises receiving data of a heart rate of the person; receiving data of a posture of the person; determining that a first posture of the person satisfies first posture criteria for a first predetermined time period; determining a first heart rate for the person during the first predetermined time period; subsequent to determining that the first posture of the person satisfies first posture criteria for a first predetermined time period, determining that a second posture of the person satisfies second posture criteria for at least a second predetermined period; determining a second heart rate for the person during the second predetermined time period; determining a change in heart rate as the second heart rate minus the first average heart rate; determining a first probability of dehydration based, at least in part, on the change in heart rate; and outputting the first probability of dehydration.

19 Claims, 4 Drawing Sheets

(56) References Cited

U.S. PATENT DOCUMENTS

| | | | |
|---|---|---|---|
| 8,343,049 B2* | 1/2013 | Hatlestad et al. | 600/301 |
| 2002/0058877 A1* | 5/2002 | Baumann et al. | 600/485 |
| 2003/0158471 A1* | 8/2003 | Narimatsu et al. | 600/321 |
| 2004/0215263 A1* | 10/2004 | Virag et al. | 607/17 |
| 2005/0103129 A1* | 5/2005 | Karason | 73/865.1 |
| 2005/0251051 A1* | 11/2005 | Pougatchev et al. | 600/485 |
| 2006/0100534 A1* | 5/2006 | Colombo et al. | 600/513 |
| 2007/0129622 A1* | 6/2007 | Bourget et al. | 600/382 |
| 2007/0161912 A1* | 7/2007 | Zhang et al. | 600/483 |
| 2007/0213619 A1* | 9/2007 | Linder | 600/481 |
| 2008/0200819 A1* | 8/2008 | Lynn et al. | 600/485 |
| 2009/0088821 A1* | 4/2009 | Abrahamson | 607/60 |
| 2010/0049070 A1* | 2/2010 | Kao et al. | 600/521 |
| 2010/0262026 A1* | 10/2010 | Meftah et al. | 600/509 |
| 2010/0268040 A1* | 10/2010 | Ben-Oren et al. | 600/301 |
| 2011/0021928 A1* | 1/2011 | Giovangrandi et al. | 600/484 |
| 2011/0112442 A1* | 5/2011 | Meger et al. | 600/595 |
| 2011/0263950 A1* | 10/2011 | Larson et al. | 600/301 |
| 2013/0079617 A1* | 3/2013 | Anderson et al. | 600/381 |

OTHER PUBLICATIONS

Carew, S. et al; "A review of postural orthostatic tachycardia syndrome"; Europace (2009) 11, 18-25.*

Carter, R. et al; "The influence of hydration status on heart rate variability after exercise heat stress"; Journal of Thermal Biology 30 (2005) 495-502.*

Charkoudian, N.; "Influences of hydration on post-exercise cardiovascular control in humans"; Physiol (2003), 552.2, pp. 635-644.*

Deegan, M. T. et al; "A new blood pressure and heart rate signal analysis technique to assess Orthostatic Hypotension and its subtypes"; Proceedings of the 29th Annual International Conference of the IEEE EMBS Cité Internationale, Lyon, France Aug. 23-26, 2007. p. 1-4.*

El-Sayed, H. et al; "Relationship between plasma volume, carotid baroreceptor sensitivity and orthostatic tolerance"; Clinical Science (1995) 88, 462-470.*

Kranning, K. K, et al; "A Mechanistic computer simulation for human work in heat that accounts for physical and physiological effects of clothing, aerobic fitness and progressive dehydration"; J. therm. Biol. vol. 22, No. 415, pp. 331-342, 1991.*

MacWilliam J. A. "Postural effects on heart-rate and blood pressure"; Quarterly Journal of Experimental Physiology, vol. XXIII, p. 1-33, 1933.*

Mathias, C. J. et al; "Water drinking in the management of orthostatic intolerance due to orthostatic hypotension, vasovagal syncope and postural tachycardia syndrome"; European journal of Neurology, 2004, 11:613-619.*

Montain, S. J. et al.; "Influence of graded dehydration on hyperthermia and cardiovascular drift during exercise"; J Appl Physiol 73:1340-1350, 1992.*

Mukai, S. et al; "Orthostatic Hypotension"; Clin Geriatr Med 18 (2002) 253-268.*

Raj, S. S. "The Postural Tachycardia syndrome (POTS): Pathophysiology, Diagnosis and Management"; Indian Pacing and Electrophysiology Journal; 6(2): 84-99 (2006).*

Hellebrandt, F.A. et al; "Physiological Study of the Vertical Stance of Man"; Reviews Published Jul. 1, 1943 vol. 23 No. 3, p. 220-255.*

Holtzhausen, L-C. et al; "The prevalence and significance of post-exercise (postural) hypotension in ultramarathon runners"; Medicine and Science in Sports and Exercise; 27(12); 1995; p. 1595-1601.*

Johnson, D. R. et al; "Dehydration and Orthostatic Vital Signs in Women with Hyperemesis Gravidarum"; Academic Emergency Medicine; Aug. 1995; vol. 2 No. 8, p. 662-697.*

Matsushima, R. et al; "Comparison of the active standing test and head-up tilt test for diagnosis of syncope in childhood and adolescence"; Clin Auton Res (2004) 14 : 376-384.*

Rossberg, F. et al; "Initial cardiovascular response on change of posture from squatting to standing"; Eur J Appl Physiol (1988) 57:93-97.*

Smith, J. J. et al; "Hemodynamic Response to the Upright Posture"; J. Clin. Pharmacol; 1994; 34:375-386.*

Sprangers, R. L et al; "Initial blood pressure fall on stand up and exercise explained by changes in total peripheral resistance"; Journal of Applied Physiology Published Feb. 1, 1991 vol. 70 No. 2, p. 523-530.*

Tanaka, H. et al; "Cardiac Output and Blood Pressure during Active and Passive standing"; Clinical Physiology (1996) 16, p. 157-170.*

* cited by examiner

SYSTEM METHOD AND DEVICE FOR DETERMINING THE RISK OF DEHYDRATION

CROSS REFERENCE TO RELATED APPLICATIONS

This application claims priority to U.S. Provisional Application No. 61/352,293, filed Jun. 7, 2010, which is hereby incorporated by reference in its entirety for all purposes.

FIELD OF THE INVENTION

The present invention generally relates to physiological data processing and more particularly, to a system, method and device for determining the risk of dehydration of a person.

BACKGROUND OF THE INVENTION

Monitoring vital signs is traditionally done on supine patients at rest. Field based measurements are typically done with a care giver or researcher controlling the person's position (e.g., posture) and degree of movement in order to minimize movement artefacts such as orthstatic changes and effects on the body due to work effort of orientation. Normally tests are performed under various conditions in a clinic manually, using such devices as blood pressure cuffs or using treadmills and stop watches for exertion fitness tests.

Measuring vital signs over time (in the field) provides more useful information for understanding a person's physiological state. However, body position and activity level are key factors that affect a person's vital signs and hence the interpretation thereof.

Information of the biomechanical context of a person allows the person's vital signs to be measured and interpreted remotely. Biomechanical sensors include, for example, tri axial accelerometers and gyroscopes which determine the posture and activity level of a person. Biomechanical sensors which form part of, or are time synchronised to a vital sign monitor, afford the opportunity to take measurements that, until now, would not be practical or useful because the person's movement or posture could have a greater effect than the variations sought. In contrast, embodiments of the present invention can determine a normal state of the person under different activity levels and postures and hence determine an abnormal state. In addition, embodiments of the present invention may be used to determine the probability of dehydration when the person is in the field (not in the clinic) and wherein the movement and posture of the person is not directed by the clinician.

These and other advantages may be provided by one or more embodiments of the present invention.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings.

DETAILED DESCRIPTION OF ILLUSTRATIVE EMBODIMENTS

In the following description, for purposes of explanation and not limitation, specific details are set forth, such as particular networks, communication systems, computers, terminals, devices, components, techniques, sensors, algorithms, data and network protocols, software products and systems, operating systems, development interfaces, hardware, etc. in order to provide a thorough understanding of the present invention.

However, it will be apparent to one skilled in the art that the present invention may be practiced in other embodiments that depart from these specific details. Detailed descriptions of well-known networks, communication systems, sensors, algorithms, computers, terminals, devices, components, techniques, data and network protocols, software products and systems, operating systems, development interfaces, and hardware are omitted so as not to obscure the description.

A person's physiology changes based on speed of movement, level of activity and posture. Embodiments of the present invention address the issue of automatically testing various physiological states when using sensors for short term and long term (in the field) monitoring of bioelectric signals of a person. When a person is remote, the clinician or coach cannot make a manual assessment of the person's posture or the time at which a certain event occurred. Some embodiments of the present invention provide a method to remotely determine these values by using a combination of biomechanical sensors, physiological sensors and algorithms that process these values over time. This specific example embodiment determines the probability of dehydration based on such values.

Determining dehydration in a person can be done via chemical means and test protocols such as orthostatic load analysis. The problem with chemical analysis is that each test stick, such as the Bayer® Q10 test strips, is that one stick per test is required and people require privacy to produce the urine sample. The problem with a traditional orthostatic tilt test is that a person must be timed manually; using a watch or clock and instructing the person throughout the test and recording heart rate data. These test systems do not lend themselves to multi person remote testing where the clinician or medical person is not present.

Some embodiments of the present invention use one or more activity sensors and one or more posture sensors along with a heart rate sensor. A single sensor module that uses the same accelerometers may be employed to provide raw data, which is processed by software that separately outputs posture and activity data (e.g., level). When a sequence of postures is detected, the measured heart rates can be used to determine the risk of dehydration.

Figure 3:
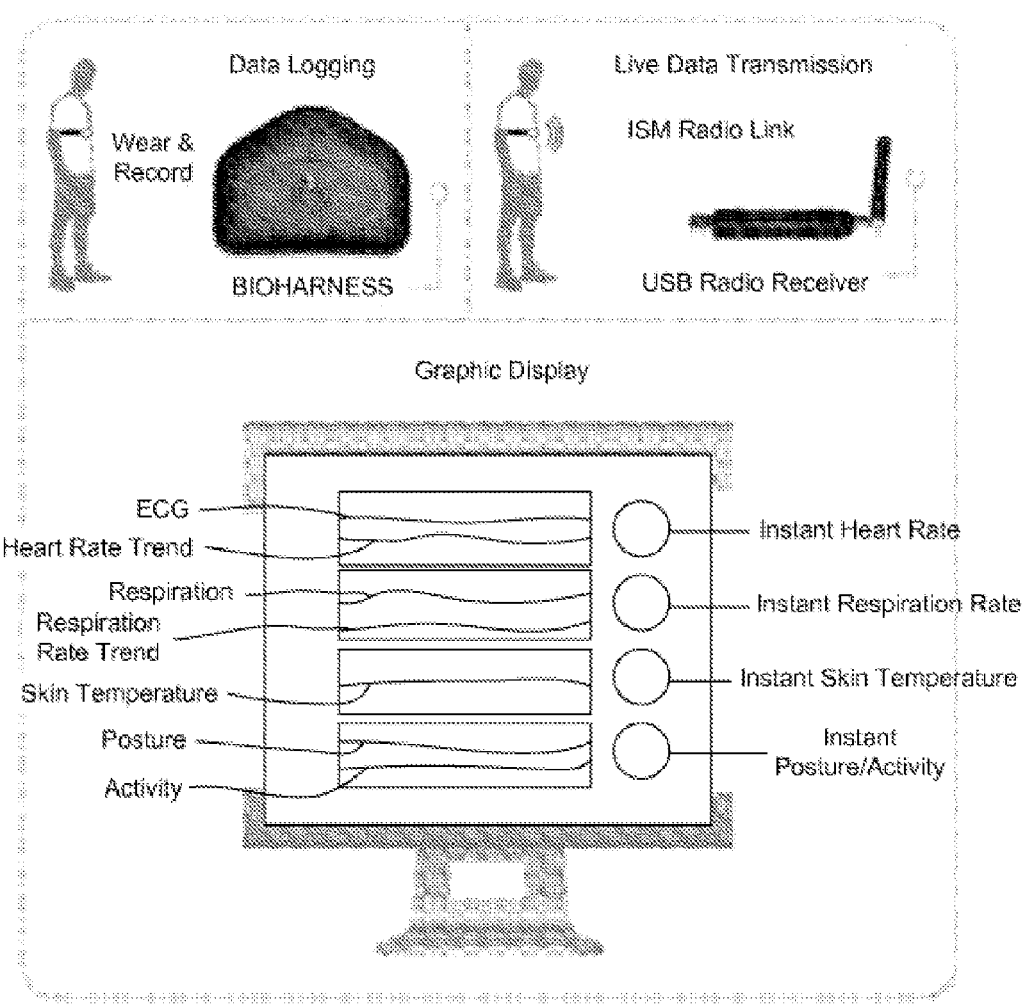
FIG. 3 depicts a BioHarness that may be used to collect (and process data), in accordance with an example embodiment of the present invention.
Figure 4:
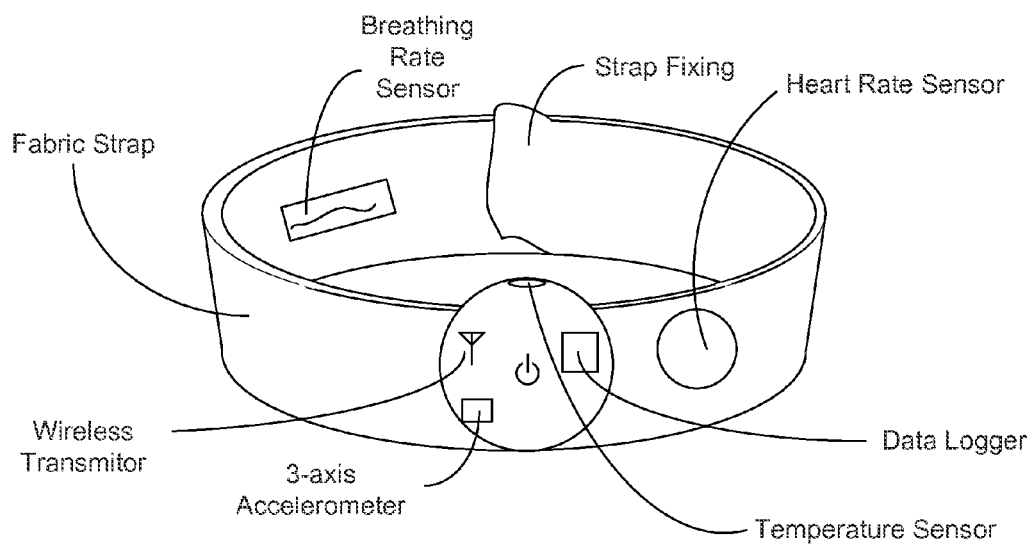
FIG. 4 depicts a BioHarness that may be used to collect (and process data), in accordance with an example embodiment of the present invention.

The data used by embodiments of the present invention may be collected and processed by a device called the Bio-Harness, which is commercially available and manufactured by Zephyr Technology of Annapolis, Md. See FIGS. 3 and 4. The device measures heart rate, breathing rate, temperature, activity and posture, is battery powered and worn as a chest strap. It includes a Bluetooth wireless transceiver and internal memory. The person may wear the device at home and/or at work (as well as in a clinic environment). The data from the biomechanical and physiological sensors (and in some embodiments environmental sensors) is regularly collected and stored in memory. Upon detection of certain physiological data (an acceptable activity and posture envelope), the algorithm processes the stored data to determine the risk of dehydration for the person. The algorithm may be executed by a processor resident in the collection device (e.g., the BioHarness) or a computer that receives the data from the collection device.

The sensor module and algorithm of this example embodiment determine (automatically) when a person is laying or sitting for a predetermined duration and when they stand for a predetermined duration. If the durations and level of activity are within acceptable limits then the delta (change in) heart rate is used to determine orthostatic loading and hence the degree of hydration. Other personal physiological parameters and environmental parameters and base lines can be used to further increase accuracy of the process.

Figure 1:
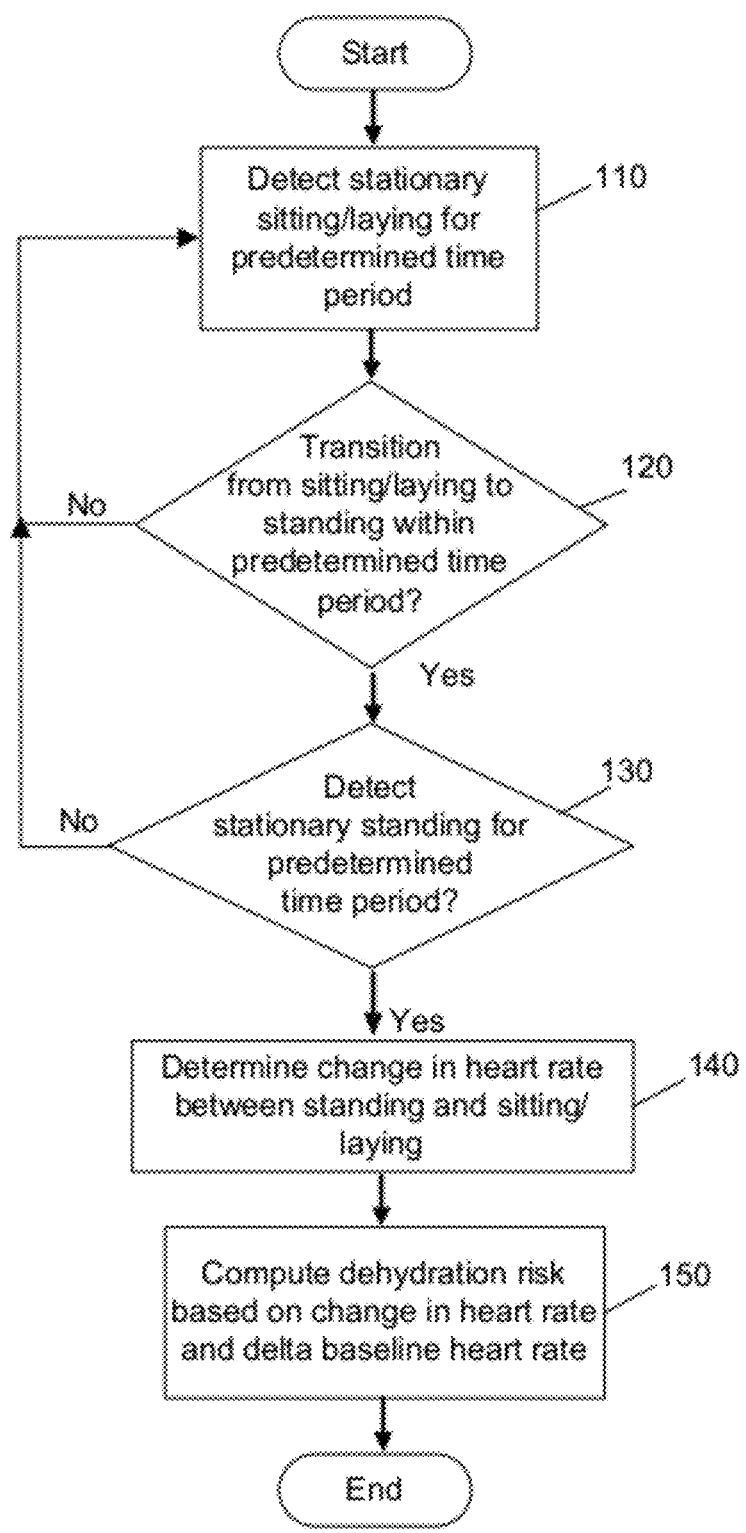
FIG. 1 is a flow chart of a process, in accordance with an example embodiment of the present invention.
Figure 2:
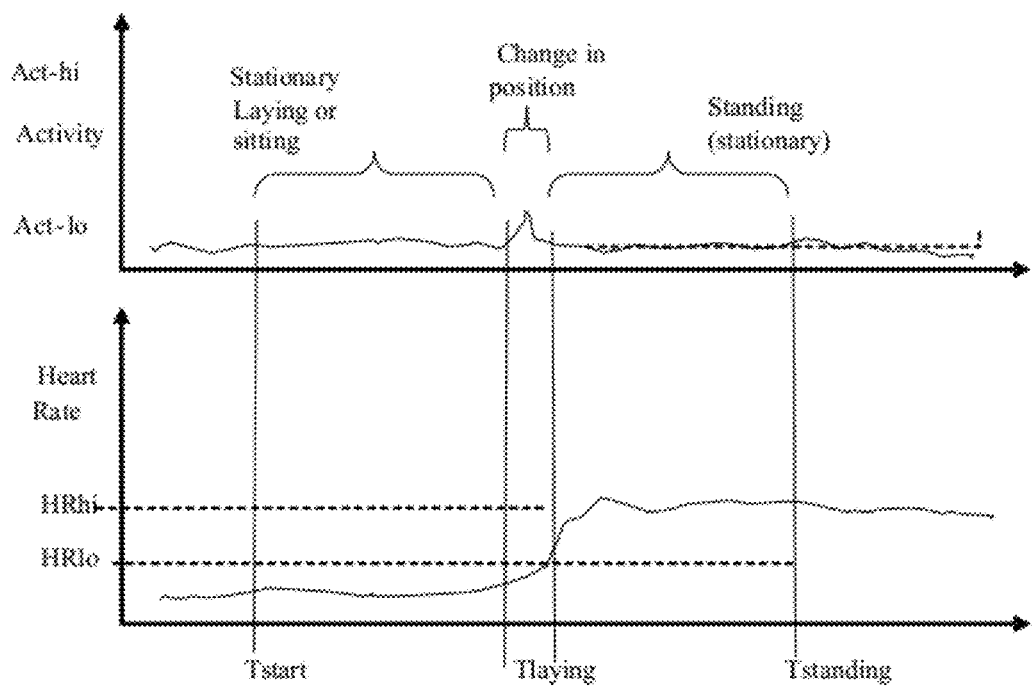
FIG. 2 is a graphic representation of heart rate and postures, in accordance with an example embodiment of the present invention.

One example algorithm for computing the risk of dehydration is described below in conjunction with FIGS. 1 and 2. The person under test may wear the BioHarness or other collection device(s) to continually (or regularly) monitor the person's heart rate, posture and other physiological data. The person's movement need not be instructed (e.g., movement of the person may simply comprise the movement as he or she performs normal activities) and processing of the data to determine the risk of dehydration may be performed when the sequence of the person's postures satisfies certain parameters. As discussed above, data of the person's posture, activity (whether stationary or not), and heart rate is continually monitored and stored. When the person's posture and activity level satisfies a triggering envelope (FIG. 2), the stored heart rate data is processed to determine the risk of dehydration. More specifically:

1. First, the system detects that the person has been in a stationary sitting or laying position for at least a first predetermined time period, followed by a transition to a stationary standing position. As discussed, the heart rate is monitored and a variable (HRlo) is set to the peak or average heart rate during the stationary sitting or laying period. Typically, the first time period will be between one and twenty minutes and may be a configuration set by the operator.
 2. Next, the system determines whether the transition from stationary sitting or laying to stationary standing occurred within a second predetermined time period. If the transition does not occur within the second predetermined time period, the process returns to detect sitting or laying for a first predetermined time period. Typically, the (maximum) second time period is between fifteen and thirty seconds.
 3. If the system determines that the transition from sitting or laying to standing occurred within the second predetermined time period, the system determines whether the person was standing for a third predetermined time period. If not the process restarts. Typically, the third time period is between one and twenty minutes.
 4. If the system determines that the person is stationary standing for the third predetermined time period, a second variable (HRhi) is set to the average measured heart rate during third time period.
 5. Next, the system calculates the change in heart rate between standing and laying (or sitting) as delta heart rate computed has HRhi minus HRlo (or HRhi−HRlo).
 6. Next the system computes the dehydration risk based on the change in heart rate and delta baseline heart rate according to the following equation:

$$\text{Dehydration risk} = K * \frac{(HRhi - HRlo)}{\text{Delta\_HR\_baseline}} \quad \text{Equation A}$$

Dehydration risk is the chance of dehydration (e.g., in percent). A dehydration risk equal to 100% indicates that there is a 100% risk of dehydration to a point greater than a predetermined percentage (e.g., 3-5%) of the person's body weight. For example a person with no acclimatization and a history of heat related illness for the risk may be 100% and an acclimatized, fully hydrated person with no heat related injury history may be 0.3 (or 30%). The "predetermined percentage of the person's body weight" for which the risk is assessed can be varied by the software application by adjusting the value of K to allow the person to be alerted at his or her (customized) desired risk of dehydration level. For example, one person may wish to know of (or be alerted to) a predetermined risk (e.g., 80% chance) of being dehydrated to 5% of their body weight and use a first value of K is used and if that person wishes to know (or be alerted to) a predetermined risk (e.g., 80%) of being dehydrated to 3% of their body weight, a second value of K would be used.

delta heart rate is an increase in heart rate by a given number (typically 20 beats per minute or bpm) between the laying and standing positions.

K is a coefficient that is changed per person based on fitness level, age weight, gender, environment, history. A medically trained person with training may change or select this number. Alternately, the system may receive inputs of various parameters (e.g., the person's age, weight, gender, fitness level, ambient temperature, etc.) and automatically compute K.

Delta_HR_baseline is the normal heart rate change for that person in a hydrated state, i.e. less than 0.5% of the person's body weight. This number is first calculated based on fitness, age, gender, weight. A baseline test with correct hydration level can be performed for further accuracy. Alternately, the value may be based on crowd sourced data for persons of that group (of age, weight, fitness level, level of exercise per week etc).

Data is automatically collected in the collection device that includes activity (via an accelerometer which measures movement in three axes), posture and heart rate. When an acceptable activity and posture envelope is detected (as illustrated by processes 110, 120, and 130 of FIG. 1), this example embodiment of the present invention computes the delta heart rate (HRhi−HRlo) at 140 and then the dehydration risk at 150 in accordance with Equation A above.

In some instances, the above computed delta heart rate may be used to determine a person's risk of dehydration and/or to improve or confirm the accuracy of Equation A. More specifically, if a person's delta heart rate is above a predetermined threshold (or simply the higher the heart rate) the person's risk of dehydration can be assessed provided any increase in heart rate is not due to panic, sweating, exercise, and/or other factor. To confirm that exercise is not influencing the person's heart rate, the heart rate may be measured only after the person is standing stationary for a predetermined time period or after the person's heart rate stabilizes for a time period (e.g., and no activity is detected). Peripheral temperature and peripheral skin sensors may be used to measure the effects of sympathetic nervous system (e.g., to ensure the person is not panicked). Similarly, the person's core temperature and whether he is sweating may also be measured (via appropriate chest sensors) to determine whether the person is hot (or overheated) or if they are experiencing vessel dilation—all of which could cause the heart to increase and therefore potentially skew any heart rate analysis. In summary, considering a person's age, fitness, weight, and/or other factors, a person's risk of dehydration may be determined based on the above computed delta heart rate (HRhi–HRlo) (which may be multiplied by one or more scaling factors) provided that other factors that might increase a person's heart rate are determined to not be influencing the person's heart rate. Thus, a person's standing (or in some instances, sitting or laying) heart rate may also be used to assess their risk of dehydration after factoring in a person's age, fitness, weight, and/or other factors, and provided that other factors that might increase a person's heart rate are determined to not be influencing the person's heart rate.

Algorithms of the present invention can be used while a person is carrying out random events (or exercises) or is performing requested (known) behaviour.

If the dehydration risk is above a predetermined threshold, a notification (an alert) may be transmitted (e.g., wirelessly) to medical personnel and an audible alarm may be sounded to alert the patient.

The present invention may be embodied, at least in part, as a computer system (one or more co-located or distributed computers) or cluster executing one or more computer programs stored on a tangible medium. The algorithm may be executed (and computer system located) local (e.g., attached to or carried by the user) or remote from the user. The algorithm may be executed on a computer system that also includes other functions such a telephone or other device (e.g., an IPhone®, IPad®, or Blackberry®), which may have processing and communications capabilities. As discussed, the algorithm may also be stored and executed on the collection device.

While the example embodiment described above determines the risk for dehydration, other embodiments instead (or additionally) may be used to determine other parameters such as a person's fitness level, the risk of heat stress, and/or other parameters.

Thus, one embodiment of the present invention comprises a method of determining a probability of dehydration of a person, that comprises receiving data of a heart rate of the person; receiving data of a posture of the person; determining that a first posture of the person satisfies first posture criteria for a first predetermined time period; determining a first heart rate for the person during the first predetermined time period; determining that a second posture of the person satisfies second posture criteria for a second predetermined period subsequent to the first posture of the person satisfying first posture criteria for the first predetermined time period; determining a second heart rate for the person during the second predetermined time period; determining a change in heart rate as the difference between the second heart rate and the first average heart rate; determining a first probability of dehydration based, at least in part, on the change in heart rate; and outputting the first probability of dehydration. The method may further include determining that an activity level of the person is below a threshold level during said second predetermined time period and/or determining a second probability of dehydration, at least in part, by comparing the second heart rate with a predetermined threshold. Determining a first probability of dehydration may comprise dividing the change in heart rate by a baseline change in heart rate. The first posture criteria may comprise sitting or laying and the second posture criteria may comprise standing (e.g., with an activity level below a threshold and/or substantially stationary). Further, the method may comprise determining that the person transitions from the first posture to the second posture within a third predetermined time period. Finally, the method may further comprise determining that the change in heart rate is above a predetermined threshold and that the increase in heart rate is not due to panic, sweating, exercise, and/or other factors of the person.

In another embodiment, the present invention comprises a method of determining a probability of dehydration of a person, that comprises receiving data of a heart rate of the person over a time period; receiving data of a posture of the person over the time period; storing in a memory data of the heart rate of the person over the time period; storing in a memory data of the posture of the person over the time period; determining that the posture of the person during the time period satisfies a similarity threshold with a posture envelope that includes a first posture and a second posture; determining a first heart rate for the person while in the first posture; determining a second heart rate for the person while in the second posture; determining a change in heart rate as a difference between the second heart rate and the first average heart rate; determining a first probability of dehydration based, at least in part, on the change in heart rate; and outputting the first probability of dehydration. The method may further comprise determining a second probability of dehydration by comparing the second heart rate with a predetermined threshold; determining that an activity level of the person is below a threshold level while the person maintains the second posture; and/or determining that the person transitions from the first posture to the second posture within a predetermined time period. Determining a first probability of dehydration may comprise dividing the change in heart rate by a baseline change in heart rate. The first posture may comprise one of sitting or laying; and the second posture may comprise standing.

Further, another embodiment of the present invention comprises a computer program product stored in a non-transitory computer readable medium and executable by a computer system to determine a probability of dehydration of a person, that comprises a code segment to determine that data of a first posture of the person satisfies first posture criteria for a first predetermined time period; a code segment to determine a first heart rate for the person during the first predetermined time period; a code segment to determine that a second posture of the person satisfies second posture criteria for a second predetermined period subsequent to the first posture of the person satisfying the first posture criteria for the first predetermined time period; a code segment to determine a second heart rate for the person during the second predetermined time period; a code segment to determine a change in heart rate a difference between the second heart rate and the first heart rate; a code segment to determine a first probability of dehydration based, at least in part, on the change in heart rate; and a code segment to output the first probability of dehydration. Determining a first probability of dehydration may comprise dividing the change in heart rate by a baseline change in heart rate. The first posture may comprise one of sitting or laying; and the second posture criteria may comprise standing. The embodiment may further comprise a code segment to determine that an activity level of the person is below a threshold level during said second predetermined time period and/or a code segment to determine that the person transitions from the first posture to the second posture within a third predetermined time period.

Thus, still another embodiment of the present invention comprises a method of determining a probability of dehydration of a person, that comprises monitoring the heart rate, activity and posture of the person; determining that the person has been in a first posture for a first predetermined time period wherein the first posture is selected from the group of sitting and laying; determining a first average (or peak) heart rate for the person while in the first posture; determining that the person transitions from the first posture to standing within a second predetermined time period; determining that the person remains standing stationary for a third predetermined time period; determining a second average heart rate (or peak) for the person while in the second posture; calculating a change in heart rate as the second average (or peak) heart rate minus the first average (or peak) heart rate; determining a first probability of dehydration by, at least in part, dividing the change in heart rate by a baseline change in heart rate; determining a second probability of dehydration by comparing the stationary standing heart rate of the person with a predetermine threshold; outputting the probability of dehydration; and providing a notification if the first or second probability of dehydration is above a predetermined threshold.

Thus, yet another embodiment of the present invention comprises a method of determining a probability of dehydration of a person, that comprises monitoring the heart rate, activity and posture of the person over a time period; storing data of the person's heart rate, activity and posture of the person over the time period; determining a first average (or peak) heart rate for the person while in the first posture; determining that the activity and posture of the person of the time period satisfies a triggering envelope; determining a second average heart rate (or peak) for the person while in the second posture; calculating a change in heart rate as the second average (or peak) heart rate minus the first average (or peak) heart rate; determining a first probability of dehydration by, at least in part, dividing the change in heart rate by a baseline change in heart rate; determining a second probability of dehydration by comparing the stationary standing heart rate of the person with a predetermine threshold; outputting the probability of dehydration; and providing a notification if the first or second probability of dehydration is above a predetermined threshold.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. A method comprising:
   receiving heart rate data associated with a heart rate of a person from a first sensor configured to be worn externally on a body of the person;
   receiving posture data associated with a posture of the person from a second sensor;
   determining, via a processor, that a first posture of the person satisfies a first posture criteria for a first predetermined time period;
   determining, via the processor, a first heart rate for the person based on the heart rate data, the first heart rate associated with the first predetermined time period;
   determining, via the processor, that the posture of the person transitions from the first posture to a second posture within a second time period after the first predetermined time period;
   if the length of the second time period is within a predetermined time period:
      determining, via the processor, that the second posture of the person satisfies a second posture criteria for a third time period, the third time period being after the second time period;
      determining, via the processor, a second heart rate for the person based on the heart rate data, the second heart rate associated with the third time period;
      determining, via the processor, a change in heart rate based on a difference between the second heart rate and the first heart rate; and
      determining, via the processor, a probability of dehydration based, at least in part, on the change in heart rate.

2. The method of claim 1, wherein the determining the probability of dehydration includes dividing the change in heart rate by a baseline change in heart rate.

3. The method of claim 1, further comprising:
   comparing the second heart rate with a heart rate threshold; and
   outputting a signal configured to alert the person of the probability of dehydration when the probability of dehydration exceeds a dehydration risk threshold and when the second heart rate is below the heart rate threshold.

4. The method of claim 1, wherein said first posture criteria is associated with sitting.

5. The method of claim 1, wherein the first posture criteria is associated with laying down.

6. The method of claim 1, wherein the first posture criteria is associated with at least one of sitting or laying down, and the second posture criteria is associated with standing.

7. The method of claim 1 further comprising:
   determining, using data received from at least a third sensor coupled with the body of the person, whether the person is experiencing panic or is perspiring, or determining an activity level of the person during the third time period; and
   outputting a signal configured to alert the person of the probability of dehydration when the probability of dehydration exceeds a dehydration risk threshold and when the person is experiencing panic or is perspiring, or the activity level is below an activity threshold.

8. A computer program stored in a non-transitory computer readable medium and executable by a computer system, the computer program comprising code to cause the computer system to:
   determine that a first posture of a person satisfies a first posture criteria during a first predetermined time period;
   determine a first heart rate of the person associated with the first predetermined time period;
   determine that the posture of the person transitions from the first posture to a second posture within a second time period after the first predetermined time period;
   if the length of the second time period is within a predetermined time period, the computer program further comprising code to cause the computer system to:
      determine that the second posture of the person satisfies a second posture criteria for a third time period, the third time period being after the second time period;

determine a second heart rate of the person associated with the third time period;

determine an activity level of the person associated with the third time period;

determine a change in heart rate, the change in heart rate being a difference between the second heart rate and the first heart rate;

determine a probability of dehydration based, at least in part, on the change in heart rate; and output an alert configured to alert the person of the probability of dehydration when the probability of dehydration exceeds a dehydration risk threshold and when the activity level of the person associated with the third time period is below an activity threshold.

9. The computer program of claim 8, wherein the code to cause the computer system to determine the probability of dehydration includes code to cause the computer system to divide the change in heart rate by a baseline change in heart rate.

10. The computer program of claim 8, wherein the first posture criteria is associated with at least one of sitting or laying down, and the second posture criteria is associated with standing.

11. The computer program of claim 8, wherein the code to cause the computer system to determine the first heart rate includes code to cause the computer system to determine the first heart rate based on heart rate data received from a sensor configured to be worn externally on a body of the person.

12. The computer program of claim 8, wherein the activity threshold is configured to prevent the alert from being output when the activity level of the person is elevated above the activity threshold due to exercise.

13. A method, comprising:

receiving, from a first sensor, an indication of a first posture of a person during a first predetermined time period;

determining, via a processor, a first heart rate of the person, the first heart rate being associated with the first predetermined time period and based on heart rate data received from a second sensor configured to be worn externally on a body of the person;

receiving, from the first sensor, an indication of a transition of the person from the first posture to a second posture during a second time period, the second time period being after the first predetermined time period;

if the length of the second time period is within a predetermined time period:

determining, via the processor, that the second posture of the person satisfies a second posture criteria for a third time period, the third time period being after the second time period;

determining, via the processor, a second heart rate of the person associated with the third time period, the second heart rate determined based on heart rate data received from the second sensor;

determining, via the processor, a probability of dehydration based, at least in part, on the first heart rate and the second heart rate.

14. The method of claim 13, wherein the determining the probability of dehydration is based, at least in part, on dividing a difference between the first heart rate and the second heart rate by a baseline change in heart rate.

15. The method of claim 13, further comprising:

comparing the second heart rate with a heart rate threshold; and outputting the probability of dehydration when the second heart rate is below the heart rate threshold.

16. The method of claim 13, wherein the indication of the transition of the person from the first posture to the second posture is associated with the person moving from at least one of sitting or laying down to standing.

17. The method of claim 13, wherein at least one of the indication of the first posture or the indication of the transition of the person from the first posture to the second posture is received from an accelerometer.

18. The method of claim 13, wherein the determining the probability of dehydration is based, at least in part, on dividing a difference between the first heart rate and the second heart rate by a baseline change in heart rate, the baseline change in heart rate associated with at least one of an age, a weight, a gender, a fitness level, or an ambient temperature.

19. The method of claim 13, further comprising transmitting a wireless signal when the probability of dehydration exceeds a threshold.

* * * * *